United States Patent
Zhang et al.

(10) Patent No.: US 9,085,505 B2
(45) Date of Patent: Jul. 21, 2015

(54) PROCESS FOR HIGHLY EFFICIENT CATALYTIC CONVERSION OF CELLULOSE RAW MATERIAL TO DIOL

(71) Applicant: DALIAN INSTITUTE OF CHEMICAL PHYSICS, CHINESE ACADEMY OF SCIENCES, Dalian, Liaoning (CN)

(72) Inventors: Tao Zhang, Liaoning (CN); Jifeng Pang, Liaoning (CN); Mingyuan Zheng, Liaoning (CN); Yu Jiang, Liaoning (CN); Aiqin Wang, Liaoning (CN)

(73) Assignee: DALIAN INSTITUTE OF CHEMICAL PHYSICS, CHINESE ACADEMY OF SCIENCES, Dalian, Liaoning (CN)

( * ) Notice: Subject to any disclaimer, the term of this patent is extended or adjusted under 35 U.S.C. 154(b) by 0 days.

(21) Appl. No.: 14/388,086

(22) PCT Filed: May 16, 2013

(86) PCT No.: PCT/CN2013/075727
§ 371 (c)(1),
(2) Date: Sep. 25, 2014

(87) PCT Pub. No.: WO2013/170767
PCT Pub. Date: Nov. 21, 2013

(65) Prior Publication Data
US 2015/0057469 A1 Feb. 26, 2015

(30) Foreign Application Priority Data
May 18, 2012 (CN) .......................... 2012 1 0159055

(51) Int. Cl.
*C07C 29/132* (2006.01)
(52) U.S. Cl.
CPC .................................. *C07C 29/132* (2013.01)

(58) Field of Classification Search
CPC ....................................................... C07C 29/132
USPC ................................................... 568/852, 861
See application file for complete search history.

(56) References Cited

FOREIGN PATENT DOCUMENTS

| CN | 101723802 A | 6/2010 |
| CN | 101768050 A | 7/2010 |
| CN | 102190562 A | 9/2011 |

OTHER PUBLICATIONS

Na Ji et al., "Direct catalytic conversion of cellulose into ethylene glycol using nickel-promoted tungsten carbide catalysts." Angewandte Chemie International Edition, Oct. 20, 2008, vol. (47), Issue 44, pp. 8510-8513.
Ming-Yuan Zheng et al., "Transition metal-tungsten bimetallic catalysts for the conversion of cellulose into ethylene glycol." ChemSusChem, Jan. 25, 2010, vol. (3), Issue 1, pp. 63-66.

*Primary Examiner* — Sikarl Witherspoon
(74) *Attorney, Agent, or Firm* — Novick, Kim & Lee, PLLC; Allen Xue

(57) ABSTRACT

This invention provides a method for highly efficient catalytic conversion of cellulosic raw materials to glycols. In the process, cellulosic compounds such as crop stalk, wood powder and etc., as feedstock are subjected to one-step catalytic conversion with a ternary composite catalyst composed of organic acid or inorganic acid which does not contain tungsten, a transition metal from Groups 8, 9 or 10 such as iron, cobalt, nickel, ruthenium, rhodium, palladium, iridium, and platinum, or a mixture thereof, and a tungsten oxide, a tungsten sulfide, a tungsten chloride, a tungsten hydroxide, tungsten bronze, tungstic acid, a tungstate, a metatungstate acid, a metatungstate, a paratungstate acid, a paratungstate, a peroxotungstic acid, pertungstate and heteropoly tungstate, or a mixture thereof. The reaction is carried out under hydrothermal conditions at a temperature between 120-300° C. with hydrogen pressure between 1-13 MPa.

8 Claims, No Drawings

PROCESS FOR HIGHLY EFFICIENT CATALYTIC CONVERSION OF CELLULOSE RAW MATERIAL TO DIOL

BACKGROUND OF THE INVENTION

1. Field of the Invention

The invention relates to a high-efficiency method for producing glycols from cellulosic materials, and more particularly to a method for catalytically producing glycols from cellulosic materials with ternary catalysts under hydrothermal conditions.

2. Description of the Related Art

Ethylene glycol and 1,2-propylene glycol are important energy liquid fuels, and also important feedstock for the synthesis of polyesters, such as poly(ethylene terephthalate), poly(ethylene naphthalate) and unsaturated polyester resin. They are also used as antifreeze, lubricant, plasticizer, surfactant and etc., and to be feedstock for organic chemical engineering with wide applications.

Producing glycols with renewable biomass can reduce human dependence on fossil energy resources, and contributes to achieving environmentally benign and sustainable development of economy. Cellulosic biomass, including carbohydrates $C_n(H_2O)_m$ of cellulose, hemicellulose, crop straw, corn cob, rice stalk, wheat stalk, miscanthus, pine wood, birch wood, and aspen wood etc., are abundant in nature. With the development of agricultural technologies, the productivity of cellulosic biomass is increasing. Producing glycols using cellulosic biomass not only reduces dependence on the petroleum resource to some extent, but also realize further processing of agricultural products for value-added chemicals.

At present, ethylene glycol can be obtained by catalytic hydrogenation of cellulose under hydrothermal conditions (Literature 1: Direct catalytic conversion of cellulose into ethylene glycol using nickel-promoted tungsten carbide catalysts, Angew. Chem. Int. Ed. 2008, 47, 8510-8513; Literature 2: Transition metal-tungsten bimetallic catalysts for the conversion of cellulose into ethylene glycol, ChemSusChem 2010, 3, 63-66: Literature 3; CN 101735014 A, Method for producing ethylene glycol from carbohydrate compounds; Literature 4: CN 102190562 A, Method for producing ethylene glycol from carbohydrate compounds). These methods employ tungsten-based catalysts and hydrogenation catalysts as composite catalysts for cellulose conversion, and obtain the ethylene glycol at yields of 60-75%. Similarly, by using binary catalysts of oxidized-status tungsten and hydrogenation catalysts, cellulose, starch and the compounds containing sugars could be efficiently converted into ethylene glycol and 1,2-propylene glycol under hydrothermal and hydrogenating conditions (Literature 5: Method for producing ethylene glycol from polyhydroxy compounds WO2011113281A).

These processes give high ethylene glycol yield and selectivity. However, under high concentration of feedstock or with different feedstock, the reaction time has to be remarkably prolonged and leads to the low efficiency of reaction; Meanwhile, because partial products readily undergo degradation in the presence of catalysts, and eventually influenced glycols yields.

In this invention, a method is provided to realize direct conversion of cellulosic materials feedstock into glycols, including ethylene glycol and 1,2-propylene glycol, in the presence of ternary catalysts of inorganic or organic acids, transition metals of Groups 8, 9 or 10 and tungsten-based catalysts. This invention is not only readily to operate with low cost, but also significantly increases the efficiency of catalytic transformation of cellulosic feedstock as well as the space time yield of glycols.

SUMMARY OF THE INVENTION

The invention provides a rapid and high efficiency method for catalytic transformation of cellulosic materials to glycols including ethylene glycol and 1,2-propylene glycol. Compared with the conventional process, this method can produce glycols with higher space time yield and fewer by-products, and is more convenient to be industrialized.

To achieve the above objective, in accordance with one embodiment of the invention, cellulosic materials, including cellulose, hemicellulose, jerusalem artichoke, crop stalk, corn cob, rice stalk, wheat stalk, pine wood, birch wood and aspen wood, are used as feedstock and transformed in water in sealed high pressure autoclave by catalytic hydrogenation. In a class of this embodiment, the catalyst is a composite catalyst, which comprises catalyst A, catalyst B and catalyst C. The catalyst A is organic acid or inorganic acid which does not contain tungsten; the active ingredient of catalyst B comprises a transition metal of Groups 8, 9 or 10 selected from iron, cobalt, nickel, ruthenium, rhodium, palladium, iridium, and platinum, or a mixture thereof; the active ingredient of catalyst C comprises metallic tungsten, tungsten nitride, tungsten carbide, tungsten phosphide, tungsten oxide, tungsten sulfide, tungsten chloride, tungsten hydroxide, tungsten bronze, tungstic acid, tungstate, metatungstate acid, metatungstate, paratungstate acid, paratungstate, peroxotungstic acid, pertungstate and heteropoly tungstate, or a mixture thereof. In a class of this embodiment, the reaction is conducted in an autoclave with stirring; the hydrogen gas is filled in the autoclave before reaction; the reaction is conducted at temperatures higher than 120° C. for no less than 5 minutes; the initial hydrogen pressure therein at room temperature is particularly between 1 and 12 MPa; the reaction temperature is particularly between 120 and 300° C., and the reaction time is between 10 min-10 hours. In a class of this embodiment, the initial hydrogen pressure in the reactor at room temperature is particularly between 3 and 7 MPa; the reaction temperature is particularly between 200 and 270° C., and the reaction time is particularly between 30 min and 3 hours;

In a class of this embodiment, the weight concentration of catalyst A in the reaction system is between 0.005% and 5%, and the weight ratio of the active metal ingredient of catalyst B to the active ingredient of catalyst C (based on the weight of tungsten element) is between 0.02 and 3000.

In a class of this embodiment, the catalyst A is organic or inorganic acid, including acetic acid, maleic acid, butyric acid, benzene sulfonic acid, 1,4-benzene bi-sulfonic acid, benzoic acid, p-phthalic acid, salicylic acid, hydrochloric acid, sulfuric acid, nitride acid, phosphoric acid, and/or a mixture thereof; the weight ratio of catalyst A is particularly between 0.001% and 1%.

In a class of this embodiment, the catalyst B is a supported catalyst, and the carrier is selected from activated carbon, alumina, silica, silicon carbide, zirconia, zinc oxide, titanium dioxide, and/or a mixture thereof; the metallic component of the active ingredient accounts for between 0.05 and 50 wt % of the catalyst.

In a class of this embodiment, the catalyst C is a supported catalyst, and the carrier is selected from activated carbon, alumina, silica, silicon carbide, zirconia, zinc oxide, titanium dioxide, and/or a mixture thereof; the metal component of the active ingredient accounts for between 0.05 and 50 wt % of the catalyst. In a class of this embodiment, the catalyst C is non-support catalyst, including different kinds of tungsten compounds.

In a class of this embodiment, in the process of production of ethylene glycol with cellulosic materials, the feedstock and water in autoclave are in liquid or partially liquid state under reaction condition. In this condition the feedstock can be stirred, and the reactant can be heated uniformly to prevent it from local overheating and producing char; the amount of composite catalysts is catalytic amount.

In a class of this embodiment, the particular weight ratio of the active metal ingredient in catalysts B to the active ingredient in catalyst C (based on the weight of tungsten element) is between 0.1 and 100; the particular weight ratio of catalyst A to the total amount of catalyst B and catalyst C is between 0.00001:1 and 1:1.

Advantages of the invention are summarized below:

1) The invention uses renewable cellulosic materials, including cellulose, hemicellulose, crop stalk, corn cob, rice stalk, wheat stalk, pine wood, birch wood and aspen wood as feedstock, which is an abundant resource and does not compete with food supply. Moreover, most of feedstock is agriculture waste. Compared with ethylene, the current feedstock of industrial process for ethylene glycol production, the feedstock of this process is renewable, thereby satisfies the requirement of sustainable development and has great significance for the waste utilization and increasing the income of farmer.

2) The method of the invention shows high conversion efficiency in the presence of composite catalyst; the selectivity of ethylene glycol is high with elevated space time yield and the process is readily to be implemented in an industrial scale.

DETAILED DESCRIPTION OF THE EMBODIMENTS

For further illustrating the invention, experiments detailing are described below. It should be noted that the following examples are intended to describe but not to limit the invention.

Example 1

Catalytic conversion experiment: 5 g cellulosic material, 0.4 g ternary catalysts and 50 mL water were put in the 100 ml autoclave. After flushing with hydrogen for three times, the reactor was pressurized with 5 MPa hydrogen, and then the temperature was increased to 245° C. and kept for 120 min reaction. After reaction, the autoclave was cooled to room temperature. The liquid products were separated from catalysts by centrifugation. The liquid products were analyzed with high performance liquid chromatography with calcium ion-exchange column, the product yields of ethylene glycol and 1,2-propylene glycol are calculated. Meanwhile, the overall gas yield of $CO_2$, $CH_4$, and $C_2H_6$ etc. is also calculated.

Example 2

Catalytic conversion of corn stalk into glycols with different ternary catalysts, the reaction conditions are the same to that of example 1 (Table 1).

TABLE 1

Catalytic conversion of corn stalk into glycols with different ternary catalysts (The weight ratio of acid to the 5%Ru/AC and tungsten acid is 0.001:1:3, the weight concentration of corn stalk is 10%).

| Acid | ethylene glycol yield/% | 1,2-propylene glycol yield/% | gas/% |
| --- | --- | --- | --- |
| — | 20.8 | 7.8 | 5.5 |
| hydrochloric acid | 37.5 | 9.2 | 4.6 |
| sulfuric acid | 40.2 | 8.9 | 6.1 |
| nitride acid | 30.1 | 6.2 | 4.9 |
| acetic acid | 32.4 | 5.1 | 8.3 |
| benzoic acid | 33.7 | 8.6 | 8.1 |
| benzene sulfonic acid | 38.5 | 8.8 | 5.7 |

As shown in the table 1, comparing the results of ethylene glycol yield in 120 min reaction with or without addition of different acid, one may find that the addition of acid greatly promoted the yield of ethylene glycol. In the presence of low concentration sulfuric acid in the reaction solution, the yield of ethylene glycol reached 40.2%.

Example 3

Catalytic conversion of different cellulosic feedstock into glycols (Table 2), the reaction conditions are the same to that in example 1.

TABLE 2

Catalytic conversion of different cellulosic feedstock into glycols (the catalysts are composite of hydrochloric acid, 5%Ru/AC and tungsten acid, the weight ratio of hydrochloric acid, 5%Ru/AC and tungsten acid is 0.001:1:3, the weight concentration of feedstock is 10%)

| Cellulosic feedstock | ethylene glycol yield/% | 1,2-propylene glycol yield/% | Gas/% |
| --- | --- | --- | --- |
| Corn stalk | 37.5 | 8.2 | 4.6 |
| Rice stalk | 35.9 | 6.7 | 5.1 |
| *Miscanthus* | 36.1 | 8.9 | 7.9 |
| Pine wood | 40.3 | 4.3 | 9.2 |
| aspen wood | 44.1 | 3.9 | 8.7 |
| white birch | 45.3 | 4.5 | 7.1 |

As shown in the table 2, the yield of glycols changed greatly among different cellulosic feedstock, and the yield of ethylene glycol was maximized to 45.3% with birch wood as cellulosic feedstock.

Example 4

Catalytic conversion of birch wood into glycols with different ternary catalysts (Table 3), the reaction conditions are the same to that in example 1.

TABLE 3 catalytic conversion of birch wood into glycols with different ternary catalysts (the weight ratio of the catalysts A, B, C is 0.001:1:3, the weight concentration of feedstock is 10%)

| Catalysts | ethylene glycol yield/% | 1,2-propylene glycol yield/% | Gas/% |
| --- | --- | --- | --- |
| hydrochloric acid + Ir/AC + $WO_3$ | 38.2 | 4.1 | 7.9 |
| hydrochloric acid + Pt/AC + tungstic acid | 32.4 | 6.8 | 9.1 |
| hydrochloric acid + IrPt/AC + tungstic acid | 40.7 | 4.2 | 7.6 |

TABLE 3-continued catalytic conversion of birch wood into glycols with different ternary catalysts (the weight ratio of the catalysts A, B, C is 0.001:1:3, the weight concentration of feedstock is 10%)

| Catalysts | ethylene glycol yield/% | 1,2-propylene glycol yield/% | Gas/% |
|---|---|---|---|
| hydrochloric acid + Ru/AC + tungstic acid | 44.1 | 5.3 | 7.7 |
| hydrochloric acid + Pd/SiO$_2$ + ammonium metatungstate | 38.5 | 4.6 | 8.1 |
| hydrochloric acid + PtRu/AC + tungstic acid | 46.1 | 6.5 | 7.9 |

As shown in the table 3, the composition of catalyst B and catalyst C greatly influenced the glycols yield, with composite catalyst of PtRu/AC, tungstic acid and hydrochloric acid, the ethylene glycol yield reached 46.1%.

Example 5

Comparison of complete conversion of cellulosic feedstock and time space yield of ethylene glycols with different catalysts (Table 4). The reaction conditions were the same to that in example 1, but the reaction time was changed.

TABLE 4

Comparison of complete conversion of rice stalk, ethylene glycol yield and time space yield of ethylene glycol with different catalysts (the catalysts are the composite of sulfuric acid, 5%Ru/AC and tungstic acid, the weight ratio of sulfuric acid, 5%Ru/AC and tungstic acid is X:1:3, the weight concentration of feedstock is 10%).

| X in catalysts | ethylene glycol yield/% | 1,2-propylene glycol yield/% | Rice stalk conversion time/min | Time space yield of ethylene glycol %/min |
|---|---|---|---|---|
| 0 | 15.9 | 5.6 | 30 | 0.53 |
| 0 | 20.5 | 5.1 | 120 | 0.17 |
| 0.001 | 30.1 | 6.0 | 30 | 1.00 |
| 0.001 | 38.7 | 4.2 | 60 | 0.64 |
| 0.002 | 35.2 | 4.1 | 20 | 1.76 |
| 0.002 | 39.2 | 3.9 | 40 | 0.98 |

As shown in the table 4, the ternary catalysts containing acid greatly improved the conversion efficiency of cellulosic feedstock as compared with that with the dual catalysts without acid addition, and the time space yield reached 1.76%/min.

In this invention, the ternary composite catalysts could significantly improve the reaction efficiency of concentrated cellulosic feedstock conversion, and improve the time space yield of glycols including ethylene glycol and propene glycol. Furthermore, the catalysts preparation and process operation are simple and convenient to be commercialized.

What is claimed is:

1. A method for producing glycols from cellulosic feedstock with high efficiency, wherein,
   cellulosic biomass is used as feedstock and put in the autoclave with water for the catalytic hydrogenation reaction with catalysts;
   said catalyst is a composite catalyst, comprising catalyst A, catalyst B and catalyst C; the catalyst A is organic acid or inorganic acid which does not contain tungsten element; the active ingredient of catalyst B is one or more transition metals selected from metallic iron, cobalt, nickel, ruthenium, rhodium, palladium, iridium, and platinum of Groups 8, 9 or 10 elements, or a mixture thereof; the active ingredient of catalyst C is one or more selected from metallic tungsten, tungsten nitride, tungsten carbide, tungsten phosphide, tungsten oxide, tungsten sulfide, tungsten chloride, tungsten hydroxide, tungsten bronze oxide, tungstic acid, tungstate, metatungstate acid, metatungstate, paratungstate acid, paratungstate, peroxotungstic acid, pertungstate and heteropoly tungstate; the reaction is carried out in an autoclave with stifling and hydrogen is charged into the reactor before reaction; the reaction is performed at temperatures not lower than 120° C. for no less than 5 min;
   said weight concentration of the catalyst A in the reaction system is between 0.0001% and 5%, and the weight ratio of the metallic active ingredient of catalyst B to the active ingredient of catalyst C (based on the weight of tungsten element) is between 0.02 and 3000.

2. The method of claim 1, wherein the gas of hydrogen is filled in the autoclave before reaction, and the initial hydrogen pressure is between 1 and 12 MPa at room temperature; the reaction temperature is not lower than 120° C. but lower than the thermal decomposition temperature of feedstock and products.

3. The method of claim 1, wherein the initial hydrogen pressure in said reactor is between 3 and 7 MPa at room temperature; the reaction temperature is between 200 and 270° C., and the reaction time is between 30 min and 3 hours.

4. The method of claim 1, wherein, the catalyst A is organic acid or inorganic acid comprising acetic acid, maleic acid, butyric acid, benzene sulfonic acid, 1,4-benzene bi-sulfonic acid, benzoic acid, p-phthalic acid, salicylic acid, hydrochloric acid, sulfuric acid, nitride acid, phosphoric acid, and/or a mixture thereof; the weight concentration of acid in the reaction system is between 0.001% and 1%.

5. The method of claim 1, wherein, the catalyst B is a supported catalyst, and the carrier is selected from activated carbon, alumina, silica, silicon carbide, zirconia, zinc oxide, titanium dioxide, and/or a mixture thereof; the component of the active metal ingredient accounts for between 0.05 and 50 wt % of the catalyst.

6. The method of claim 1, wherein said catalyst C is a non-supported catalyst;
   or,
   catalyst C is a supported catalyst with the carrier selected from activated carbon, alumina, silica, silicon carbide, zirconia, zinc oxide, titanium dioxide, and/or a mixture thereof; the metal component of the active ingredient accounts for between 0.05 and 50 wt % of the catalyst.

7. The method of claim 1, wherein, the feedstock of cellulosic material and water in autoclave are in liquid or partially liquid state under reaction condition, and the composite catalysts amount is catalytic amount;
   cellulosic materials comprise cellulose, hemicellulose, crop stalk, corn cob, wheat stalk, rice stalk, pine wood, white birch and aspen wood and/or a mixture thereof.

8. The method of claim 1, wherein, the weight ratio of the active metal ingredient of catalyst B to the active ingredient of catalyst C based on weight of tungsten element is between 0.1 and 100; the weight ratio of the catalyst A to the total amount of catalyst B and catalyst C is between 0.00001:1 and 1:1.

* * * * *